United States Patent [19]
Rocco

[11] Patent Number: 6,051,395
[45] Date of Patent: Apr. 18, 2000

[54] METHOD AND COMPOUND FOR DETECTING LOW LEVELS OF MICROORGANISMS

[75] Inventor: Richard M. Rocco, Mountain View, Calif.

[73] Assignee: Biometric Imaging, Inc., Mountain View, Calif.

[21] Appl. No.: 09/206,086

[22] Filed: Dec. 4, 1998

Related U.S. Application Data

[60] Provisional application No. 60/097,864, Aug. 25, 1998.

[51] Int. Cl.$^7$ .............................. C12Q 1/04; G01N 33/48; C07G 11/00
[52] U.S. Cl. .............................. 435/34; 435/63; 536/16.8
[58] Field of Search ............................ 435/34, 252.1, 435/252.4, 973; 436/172, 63; 536/13.6, 16.8; 530/319

[56] References Cited

U.S. PATENT DOCUMENTS

| | | | |
|---|---|---|---|
| 4,385,126 | 5/1983 | Chen et al. | 436/518 |
| 4,661,913 | 4/1987 | Wu et al. | 364/500 |
| 5,135,851 | 8/1992 | Kajander | 435/34 |
| 5,137,810 | 8/1992 | Sizemore et al. | 435/7.32 |
| 5,453,505 | 9/1995 | Lee et al. | 544/124 |
| 5,545,535 | 8/1996 | Roth et al. | 435/34 |
| 5,545,721 | 8/1996 | Carroll et al. | 530/391.7 |
| 5,741,657 | 4/1998 | Tsien et al. | 435/18 |
| 5,843,699 | 12/1998 | Strenkoski et al. | 435/34 |

OTHER PUBLICATIONS

Merriam Webster's Collegiate Dictionary, 10th edition, p. 50, Merriam–Webster, Inc. Springfield, MA. (1996). No Month Given.

Deng et al. Fluorescent conjugates of Brefeldin A selectively stain the endoplasmic reticulum and Golgi complex of living cells. J. Histochem. And Cytochem. 43(9), pp. 907–915. (Sep. 1995).

Drug Facts and Comparisons®, 1995 Edition, pp. 2059, 2062, 2464. Facts and Comparisons, St. Louis, MO. (1995). No Month Given.

Read et al. Enumeration of CD34+ hematopoietic progenitor cells in peripheral blood and leukapheresis products by microvolume fluorimetry: a comparison with flow cytometry. J. Hematotherapy, 6(4), 291–301. (Aug. 1997). Abstract Only.

R. Bernander et al., "Flow Cytometry of Bacterial Cells: Comparison Between Different Flow Cytometers and Different DNA Stains", *Cytometry* 31:29–36 (1998).

M. J. Rybak et al., "Combination Antimicrobial Therapy for Bacterial Infections", *Drugs* Sep. 1996 52(3), 390–405.

J. R. Johnson et al., "Direct Antimicrobial Susceptibility Testing for Acute Urinary Tract Infections in Women", *Journal of Clinical Microbiology*, vol. 33, No. 9, Sep. 1995, pp. 2316–2323.

R. S. Pore, "Antibiotic susceptibility testing by flow cytometry", *Journal of Antimicrobial Chemotherapy* (1994) 34, 613–627.

J. L. Kadurugamuwa et al., "Surface Action of Gentamicin on *Pseudomonas aeruginosa*", *Journal of Bacteriology*, vol. 175, No. 18, Sep. 1993, pp. 5798–5805.

P. Schindler et al., "Action of Polymyxin B on Bacterial Membranes: Morphological Changes in the Cytoplasm and in the Outer Membrane of *Salmonella typhimurium* and *Escherichia coli* B", *Antimicrobial Agents and Chemotherapy*, Jul. 1975, pp. 95–104.

F. A. Chen et al., "Feasibility Studies for Simultaneous Immuno–chemical Multianalyte Drug Assay by Capillary Electrophoresis with Laser–Induced Fluorescence", *Clinical Chemistry*, vol. 40, No. 9 (1994), pp. 1819–1822.

B. A. Newton, "A Fluorescent Derivative of Polymyxin: its Preparation and Use in Studying the Site of Action of the Antibiotic", *Journal of General Microbiology*, vol. 12, No. 2 (1955), pp. 226–236.

*Primary Examiner*—Ralph Gitomer
*Assistant Examiner*—Marjorie A. Moran
*Attorney, Agent, or Firm*—Thomas Schneck; David M. Schneck

[57] ABSTRACT

A method and compound for detecting low levels of microorganisms in biological samples is disclosed. In the method, an antibiotic is conjugated to a detectable label. This antibiotic/label conjugate is then introduced into a sample containing biological material. The antibiotic binds to target microorganism where the label allows for detection of localized concentrations of the antibiotic. A compound to accomplish this method is also described. This compound is an antibiotic conjugated to a fluorescent dye. This dye has an excitation and emission wavelength that are not interfered by substances typically found in biological samples.

13 Claims, 2 Drawing Sheets

1000 CFU/ml 100,000 CFU/ml

METHOD AND COMPOUND FOR DETECTING LOW LEVELS OF MICROORGANISMS

CROSS REFERENCE TO RELATED APPLICATION

This application claims priority from provisional application Ser. No. 60/097,864, filed Aug. 25, 1998.

TECHNICAL FIELD

The present invention is generally directed to the detection of low quantities of microorganisms and more particularly pertains to the use of microbial binding agents labeled with a detectable marker to detect microbes.

BACKGROUND ART

The detection of a wide variety of microorganisms in biological samples, food samples, potable water samples and pharmaceutical products is required for the effective treatment of disease and the maintenance of public health and safety. For example, platelet transfusions are often required for patients at risk from severe bleeding following myelosuppressive therapies, such as chemotherapy, or for patients with severe thrombocytopenia who undergo surgery. Platelet products are generally stored at room temperature (up to 5 days) and are thus susceptible to bacterial contamination and unrestricted bacterial growth. This is particularly relevant to platelet products that are produced by pooling of random donations. Patients that receive bacterially contaminated platelets can have severe reactions to the transfusion, especially when the patients are immunocompromised. It is estimated that 1 in 2,000 platelet bags are bacterially contaminated.

Traditional methods for evaluating bacterially contaminated platelets are based on culturing an aliquot of the platelet product for several days. Because of the time required for the culture, this procedure is often impractical for assessing products prior to transfusion given that during the several day test period any microbial colony forming units (CFU) would rapidly multiply. Only those patients appearing to have an adverse reaction to the transfusion will have their transfused product analyzed for contamination. Since this analysis occurs after the transfusion, the patients are at some medical risk. A rapid screening method for microbial contaminants would allow for screening of platelets for microbial contaminants prior to transfusion, minimizing the risks of patient infection. Despite this need, no such rapid screening method is currently commercially available.

Conventional techniques for the detection of microorganisms in suspect samples often require the growth of the microorganism in order to increase the cell numbers. Following a one to five day growth period in nutrient media, the microorganisms are detected using a wide variety of detection methods. Fluorescence labeled detection markers have increased sensitivity over conventional calorimetric marks and offer the possibility of reduced analysis times because they require less cell numbers to register a positive result. For example, a fluorescent derivative of polymyxin has been used to show binding to particular species of microorganisms. (Newton, B. A. J. gen. Microbiol. 1955) This compound was used to localize polymyxin binding in fractionated cellular components. Pure cultures of the target organisms were grown in enriched media to ensure high cell counts of target cells. Viewing the fluorophore required washing and isolation of the target cells to separate the cells from the background fluorescence and to eliminate from the target cells biological and other compounds that would interfere with the absorption or emission wavelengths of the fluorescent derivative.

More recently, fluorometric methods have been developed using a wide variety of combinations of binding agents and detectable labels. In these assays the binding agent is labeled with a fluorescent marker. The binding agent binds to the microorganism and the presence or absence of the microorganism can be determined using various fluorometric measuring devices, for example fluorescence microscopy or flow cytometry. Examples of such binding agents include antibodies, DNA/RNA probes, phage and other agents that bind to some target cell component.

Despite these improvements in technique, rapid fluorometric techniques still suffer from numerous problems. An initial problem is inadequate sensitivity and/or specificity. Heretofore used fluorescent detection methods for microorganisms which are species and sometimes genus specific can not screen for a wide variety of microorganism species in a suspect sample. For example, antibodies and nucleic acid probes with a fluorescent label are widely used, but only to screen for specific pathogens. Typical examples of such tests include specific fluorometric assays for Salmonella using antibodies and assays employing nucleic acid probes for *E. coli* 0157. To screen for all microbial contaminants in a given biological sample would require numerous assays, one for each microorganism of interest. These assays also lack adequate sensitivity. Their reported detection limits are often at 10,000 CFU/mL or more. The introduction of the polymerase chain reaction (PCR) and similar amplification techniques have greatly improved these detection limits; however they can no longer be regarded as rapid methods as they often take up to one day to complete.

Rapid fluorometric screening methods which employ a direct stain have been developed and are widely used. They too have several problems. First, direct staining often lacks sensitivity. In addition these assays can also lack specificity. Direct methods employ a stain which binds to some component or cell structure of the microorganism which causes it to take on a fluorescent signal. Wheat germ agglutinin, for example, binds to a wide variety of gram positive cell walls including red blood cells. When these compounds are conjugated with a fluorescent label they may be used for rapid detection of gram positive organisms (U.S. Pat. No. 5,137,810). Like many similar tests sensitivity is increased by removing cells from their native environment, washing the cells, and detecting the gram positive organisms on a solid support. Direct fluorometric DNA staining reagents have also been developed and are widely used. Typical of these is acridine orange. This compound is taken up into the cell where it binds specifically with nucleic acid (DNA and RNA) resulting in a characteristic fluorescent emission. These stains will stain all cells that contain DNA and extensive pre-treatment and filtration techniques have been developed to improve the specificity of these assays. More information could be gathered more rapidly with an assay capable of directly targeting within a biological sample a wide variety of microorganisms, with the ability of the assay to specifically target either specific species or broader classes of microorganisms.

It is the object of the invention to provide a method to screen biological samples and rapidly detect low levels of microorganisms. It is another object to provide a method to detect microorganisms that does not require culturing steps and minimizes the purification steps required by this method. It is a further object to provide an assay for microorganisms that can alternative- ly be either specific to a given species or genus of microbe or broad spectrum, capable of detecting an entire class of microorganisms.

Another object of the invention is to describe a novel antibiotic/fluorescent dye conjugate. The fluorescent marker used in this compound should be detectable when present in a biological sample.

SUMMARY OF THE INVENTION

The above objects are achieved by tagging microorganisms in samples with labeled antibiotics and then detecting the labels. Antibiotics of selected specificity are used as binding agents against microbes agents in biological samples. By selecting a particular antibiotic for its specificity, one imparts this specificity to the microbe detection method and hence the present screening technique. Use of a highly specific antibiotic yields a microbe detection method for use in a very specific screening process, while the use of a broad spectrum antibiotic or a cocktail of such antibiotics yields a microbe detection method for advantageous use in screening for a broad spectrum of microorganisms.

In one embodiment, fluorescent dyes are conjugated to an antibiotic to form detection agents. Particular fluorescent dyes are selected, among other considerations, for their ability to fluoresce at a wavelength not subject to interference by the presence of biological material. This requires fluorescence at 590 nm or higher, preferably above 600 nm. In other contemplated embodiments the antibiotic could be conjugated to a radioactive compound, chelating agent or other detectable agents.

Once the desired antibiotic is conjugated with the desired dye and appropriately purified, microvolume fluormetric techniques are used to detect the presence of the targeted organisms. This may entail the simple inspection of a sample through a fluorescent microscope for a qualitative result or computer enhanced image processing and analysis as provided by currently available microvolume fluorimeter systems manufactured by Biometric Imaging of Mountain View, Calif. for quantitative results.

The efficacy of the methods of the present invention in the presence of biological materials is especially advantageous in the analysis of blood and blood components, cerebral spinal fluid (CSF), urine and miscellaneous other body fluids. An important advantage of the present screening system is the ability to detect how levels of microorganisms in blood and blood products without additional steps of culturing microorganisms, binding microorganisms to filters, or refining the biological sample. The antibiotic with fluorescent label is introduced directly into the sample afterwhich it is subjected to fluorometric analysis. Such capability is similarly advantageous in the analysis of water, food products, pharmaceutical products or other samples containing biological materials that may be contaminated with microorganisms.

These and other features and advantages of the present invention will become apparent from the following detailed description of a preferred embodiment which, taken in conjunction with the accompanying drawings, illustrates by way of example the principles of the invention.

BEST MODE FOR CARRYING OUT OF THE INVENTION

Figure 1:
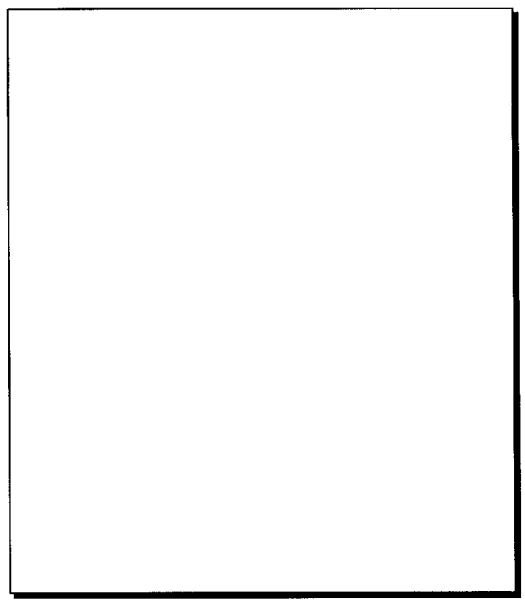
FIG. 1 is a visual image through a fluorescent microscope of a probe containing sample substantially devoid of microorganisms.

The present invention provides a technique for rapidly detecting extremely low numbers of bacteria and is capable of doing so even in biological material containing samples. Nominally, a detection limit below 1,000 CFU/mL is achievable in less than one hour. The specificity of the technique may be tailored to target a single microorganism species or to target an entire class of microorganisms.

The invention provides the use of one or more labeled agents conjugated with one or more antibiotics in combination with known detection techniques. The use of antibiotics allows the technique to be as selective or as inclusive as desired. For example, a fluorescent dye conjugated with an antibiotic is selected to fluoresce at wavelengths and have excitation wavelengths which are not subject to interference by biological materials. Since suspended particulates responsible for the turbidity of many biological samples absorb in the 200–300 nm range and since hemoglobin pigments absorb in the 400–500 nm range fluorescence outside those ranges, i.e., greater than 600 nm is preferred. The dye must also be selected based on its ability to bind with the selected antibiotic. Since many antibiotics have amino groups sufficiently distanced from the antibiotic's active sites, binding by the dye to such group has been found to be most effective and easily accomplished. Available carboxyl groups offer similar bonding opportunities. A number of fluorescent dyes that satisfy this criteria are currently commercially available.

Upon conjugation and after appropriate clean-up and separation, the fluoresently conjugated antibiotic is introduced into the sample to be tested. Because the dye is selected to fluoresce in a far infra red region, the sample may contain biological materials without adverse effect to the dye's excitation or fluorescent detection of the fluorescent label. In fact, the probe may be introduced directly into blood or blood components, CSF, urine or other bodily fluids. Water or food product samples or pharmaceutical products can be similarly tested. Within minutes, visual examination of the fluorescent image through a microscope would provide a qualitative indicator of the presence of the targeted microorganisms. Computerized image enhancement and analysis is well known in the art of microvolume fluorimetry and is capable of providing quantitative results.

While a great number of antibiotics/fluorescent label combinations satisfy the criteria of the present invention, the following descriptions are intended to merely provide representative examples thereof:

Preparation of Antibiotic/Fluorescent Label Conjugate

The preparation of a polymyxin B/Cy5™ probe is achieved as follows. Polymyxin B is a broad spectrum antibiotic readily available on a commercial scale. Cy5™, a fluorophore that absorbs at about 649 nm and fluoresces at about 670 nm, is readily available on a commercial scale from Amersham Life Sciences, Inc. of Arlington Heights, Ill. Cy5™ is available in powdered form and upon forming an aqueous solution under alkaline conditions (pH>9) its ester group will conjugate to the free amino groups of the polymyxin B. More particularly, the antibiotic is first dissolved at 1 mg/mL in a sodium carbonate-sodium bicarbonate buffer (pH~9.3) A excess amount of Cy5™ is added and the mixture is agitated occasionally for 15 minutes at room temperature taking care to avoid foaming.

After a 15 minute reaction time, the labeled antibiotic is separated from excess Cy5™ and any unlabeled antibiotic is removed by conventional methods such as by ion exchange chromatography. The chromatography column is preferably pre-equilibrated with phosphate-buffered saline while the antibiotic solution is preferably eluted using the same buffer.

After conjugation and clean-up, a stock solution of the labeled antibiotic is prepared at a concentration of 1 mg/mL in phosphate buffered saline or methanol and stored at −20° C. Methanal solutions have been found to be somewhat more stable. Alternatively, drying the methanol down to a dry condition has been found to yield a highly stable solid.

The preparation of vancomycin/BODIPY® or gentamycin/BODIPY® probes are achieved as set forth below. Both vancomycin and gentamycin are well known, commercially available broad spectrum antibiotics. BODIPY® is a fluorophore commercially available from Molecular Probes, Inc. of Eugene, Oregon that absorbs at 665 nm and fluoresces at 676 nm. The chemical name of this product is (E,E)-3,5-bis-(4-phenyl-1-3-butadienyl)-4,4-difluoro-4-bora-3a,4a-diaza-s-indacene. The dye is a sacchiamide ester that binds to the free amino groups present in the antibiotics. Conjugation and clean up is achieved as follows.

Vancomycin/BODIPY®

A sample of vancomycin HCL is dissolved in dimethylformamide which contains n,n-diisopropylethylamino. To this solution is added BODIPY® 665/676, succinimidyl ester and the whole mixture is stirred at room temperature overnight. Ether is added to the reaction mixture to precipitate the product. The resulting solid is collected by filtration. This solid is dissolved in sodium carbonate solution and subjected to a LH-20 (sephadex) column. The desired fractions are combined and lyophilized to give a dark blue solid.

Gentamycin/BODIPY®

A solution of BODIPY® 665/676, succinimidyl ester in dimethylformamide is added into an aqueous solution of gentamycin sulfate which contains sodium carbonate. After stirring at room temperature overnight, it is centrifuged to remove some precipitate. The resulting supernatant is subjected to a LH-20 (sephadex) column chromatography. It is eluted first with water and then with methanol. The desired fractions are combined and concentrated under vacuum to give a dark blue solid.

All of three of the fluorescently labeled antibiotics, the preparation of which is described above, have been found to be effective in the detection of the following microorganisms at about 1,000 CFU/mL: *Escherichia coli, Staphylococcus epidermidis, Bacillus subtilis, Pseudomonas fluorescens* type II, *Staphylococcus aureus*, and *Serratia marcescens*.

In order to enhance the broad spectrum capability of the present invention, a cocktail of probes may be prepared. Combining a plurality of broad spectrum antibiotics that display detectable fluorescence will provide an essentially all inclusive bacterial detection capability.

Validation

In order to validate the binding ability of the fluorescent dye labeled antibiotic, disc plate assay techniques are employed. A culture plate of a target microorganism is prepared after which the following are deposited and dried onto standard sterile filter paper discs thereon: (1) the antibiotic, (2) the labeled antibiotic, (3) the dye and (4) one or more controls. The binding ability of the labeled antibiotic is validated if the effect on the culture by the labeled antibiotics is similar to that of the unlabeled antibiotic. All of the above-identified antibiotic probes have been shown to have maintained their binding capacity relative to their unlabeled counterparts to bind to the target microorganisms.

Sample Preparation

Prior to conducting an analysis with a particular labeled antibiotic, the stock solution is diluted to a working concentrate of about 2.5–50 pg/mL. A 100 μL volume sample is combined with a 100 μL of Phos Buffer (pH 7.3, 0.1M) and 10 μL of probe (@ 5 μg/mL). The solution is vortexed and incubated for 15 minutes at 37° C. An additional 100 μL of the Phos buffer is added, vortexed and either applied to a slide or 50 μL thereof is loaded into a VC120 capillary for reading by an IMAGN® 2000 microvolume fluorimeter sold by Biometric Imaging of Mountain View, Calif. Alternatively, a Tris buffer (pH 7.4, 0.1M) rather than the Phos buffer is used. Alternatively, any number of well known techniques may also be employed to examine or analyze the sample. By simply examining a slide under a fluorescent microscope, a qualitative indication of the presence or absence of microorganisms is immediately ascertainable.

Figure 2:
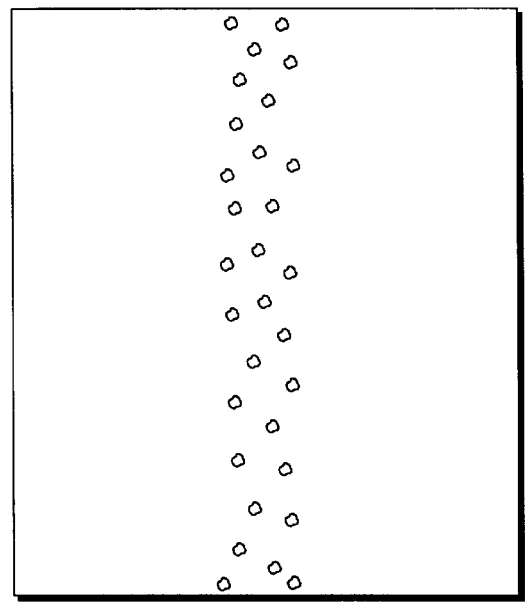
FIG. 2 is a visual image through a fluorescent microscope of a probe containing sample with microorganisms.

FIG. 1 is a visual image as seen through a fluorescent microscope of a sample of platelet concentrate (blood product intended for in vivo infusion) that has had a polymyxin B/Cy5™ probe introduced thereinto. The absence of any features in the hazy portion visible in the center of the field is representative of a negative response. In comparison thereto, FIG. 2 is a visual image of a platelet concentrate with the polymyxin B/Cy5™ probe showing a positive response to Serratia marcescens. The highlights that are clearly visible over the background haze are indicative of the presence of the microorganism and thus constitutes a positive response.

Figure 3:
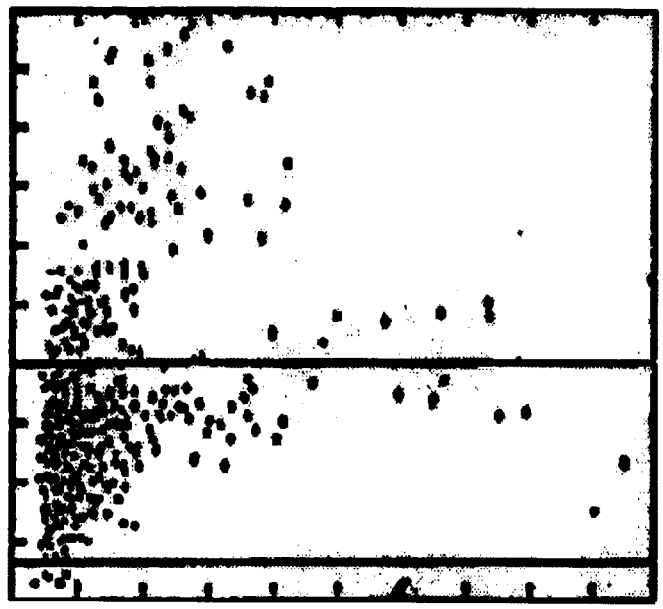
FIG. 3 is a data plot of a sample containing 1,000 CFU/mL.
Figure 4:
FIG. 4 is a data plot of a sample containing 100,000 CFU/mL.

FIG. 3 is a plot of computer analyzed data of a microorganism sample culture containing 1,000 CFU/mL as produced by an IMAGN® 2000 microvolume fluorimeter. In comparison thereto, FIG. 4 illustrates the plot of computer analyzed data of a culture with a microorganism count of 100,000 CFU/mL. The very pronounced increase in data points demonstrates the sensitivity of the technique of the present invention.

The present invention overcomes many of the shortcomings and disadvantages associated with previously used techniques for detecting the presence of microorganisms. The methods described herein enable much lower numbers of microorganisms to be detected much more rapidly than with presently used clinical assays. The specificity of the test can readily be selected to be as narrow or as broad as desired. Moreover, the sensitivity and specificity to the targeted bacteria are substantially unaffected by the presence of biological materials. Direct analysis of a biological sample is therefore possible and levels of microorganism as low as 1,000 CFU/mL are detectable in less than one hour.

I claim:

1. An assay to detect bacteria in a liquid sample containing biological material, the assay comprising:

obtaining a liquid sample containing biological material;

directly combining the liquid sample with at least one antibacterial antibiotic to form a homogenous assay mixture, wherein said antibacterial antibiotic is labeled with an optically detectable label, said label selected such that it is not subject to optical interference by biological materials; and optically detecting bacteria in the assay mixture, wherein bacteria colony forming units may be detected in a period of time less than one hour with a lower detection limit of 1000 per millimeter.

2. The assay of claim 1 further comprising, before combining the antibiotic with the liquid sample an additional step of performing an assay to determine if the antibacterial antibiotic labeled with an optically detectable label has reduced binding ability compared to an antibiotic without said label.

3. The assay of claim 1, wherein said antibiotic is a binding agent to a single species of bacteria.

4. The assay of claim 1, wherein said antibiotic is a binding agent to a group of more than one species of bacteria.

5. The assay of claim 1 wherein said bacteria are gram positive bacteria.

6. The assay of claim 1 wherein said bacteria are gram negative bacteria.

7. The assay of claim 1 wherein said optically detectable label is a fluorescent dye.

8. The assay of claim 1 where said fluorescent dye has an excitation wavelength and an emission wavelength that are 600 nm or longer.

9. The assay of claim 1, wherein the liquid sample is a fluid from a human being.

10. The assay of claim 1, wherein the liquid sample is one member of the group consisting of blood, blood components, blood products, cerebral spinal fluid, and urine.

11. The assay of claim 1 wherein the liquid sample is one member of the group consisting of food products, water and pharmaceutical products.

12. The assay of claim 1 wherein the step of optically detecting is effected by using microvolume fluorimetry to quantify bacterial colony forming units.

13. The assay of claim 1 wherein the step of optically detecting is effected by scanning the interior of a volumetric capillary containing the assay mixture.

* * * * *